United States Patent [19]

Keusch et al.

[11] Patent Number: 4,989,607

[45] Date of Patent: Feb. 5, 1991

[54] HIGHLY CONDUCTIVE NON-STRINGY ADHESIVE HYDROPHILIC GELS AND MEDICAL ELECTRODE ASSEMBLIES MANUFACTURED THEREFROM

[76] Inventors: Preston Keusch, 220 E. 84th St., Apt. 3-D, New York, N.Y. 10028; Christine A. Czap, 197 Oriol Dr., Montgomery, N.Y. 12549; Keith A. Murdock, 288 Haverstraw Rd., Suffern, N.Y. 10901; Linda Lennon, R.D. 1, Box 834, Campbell Hall, N.Y. 10916

[21] Appl. No.: 330,669

[22] Filed: Mar. 30, 1989

[51] Int. Cl.$^5$ .................... A61B 5/0402; A61N 1/04
[52] U.S. Cl. ..................... 128/640; 128/798; 128/802; 252/500
[58] Field of Search ............... 128/639-641, 128/798, 802, 803; 252/500

[56] References Cited

U.S. PATENT DOCUMENTS

| | | |
|---|---|---|
| 3,065,770 | 11/1962 | Libansky . |
| 3,264,202 | 8/1966 | King . |
| 3,357,930 | 12/1967 | Marks . |
| 3,419,006 | 12/1968 | King . |
| 3,822,238 | 7/1974 | Hudgin . |
| 3,898,143 | 8/1975 | King . |
| 3,900,378 | 8/1975 | Osterholtz . |
| 3,911,906 | 10/1975 | Reinhold . |
| 3,993,049 | 11/1976 | Kater . |
| 3,993,551 | 11/1976 | King . |
| 3,993,552 | 11/1976 | King . |
| 3,993,553 | 11/1976 | King . |
| 3,994,302 | 11/1976 | Brennen . |
| 3,998,215 | 12/1976 | Gumbusky . |
| 4,008,721 | 2/1977 | Burton . |
| 4,054,714 | 10/1977 | Mastrangela . |
| 4,066,078 | 1/1978 | Berg . |
| 4,067,342 | 1/1978 | Burton . |
| 4,092,985 | 6/1978 | Kaufman . |
| 4,094,822 | 6/1978 | Kater ................. 252/518 X |
| 4,109,648 | 8/1978 | Larke et al. . |
| 4,125,110 | 11/1978 | Hymes . |
| 4,141,366 | 2/1979 | Gray . |
| 4,156,066 | 5/1979 | Gould . |
| 4,156,067 | 5/1979 | Gould . |
| 4,192,827 | 3/1980 | Good . |
| 4,273,135 | 6/1981 | Heilmann . |
| 4,274,420 | 6/1981 | Hymes . |
| 4,300,575 | 11/1981 | Wilson . |
| 4,317,278 | 3/1982 | Lowe . |
| 4,318,746 | 3/1982 | Osipow . |
| 4,362,165 | 12/1982 | Carmon et al. . |
| 4,365,634 | 12/1982 | Robinson . |
| 4,383,529 | 5/1983 | Webster . |
| 4,393,584 | 7/1983 | Robinson . |
| 4,458,696 | 7/1984 | Larimore . |
| 4,515,162 | 5/1985 | Yamamoto et al. . |
| 4,522,223 | 1/1986 | Balsy et al. . |
| 4,524,087 | 6/1985 | Engel . |
| 4,539,996 | 9/1985 | Engel . |
| 4,543,958 | 10/1985 | Cartmell . |
| 4,554,924 | 11/1985 | Engel . |
| 4,593,053 | 6/1986 | Jevine et al. . |
| 4,684,558 | 8/1987 | Essmyer . |
| 4,699,146 | 10/1987 | Sieverding .............. 128/798 |
| 4,706,680 | 11/1987 | Keusch et al. ............ 128/641 |
| 4,750,482 | 6/1988 | Sieverding . |
| 4,777,954 | 10/1988 | Essmyer . |
| 4,860,754 | 8/1989 | Sharik et al. ............ 128/640 |

FOREIGN PATENT DOCUMENTS 0012402  6/1980  European Pat. Off. ............ 128/639
83305770.6  5/1985  European Pat. Off. .

*Primary Examiner*—Lee S. Cohen

[57] ABSTRACT

The highly conductive hydrogels of this invention are comprised of a cohesive uniform mixture of poly(vinyl pyrrolidone), a viscosity-enhancing hydrophilic polymer, and an effective amount of an electrolyte. This polymeric mixture which is crosslinked by exposure to radiant energy provides a gel-like solid which is sufficiently tacky and adhesive to adhere to the subjects' skin and yet is substantially non-stringy and non-aggressive such that the use of such hydrogel imparts less discomfort to the user. In addition, the consumer utilizing the product of this invention would not experience the objectionable sticky, stringy sensation associated with existing conductive adhesive gels.

39 Claims, No Drawings

HIGHLY CONDUCTIVE NON-STRINGY ADHESIVE HYDROPHILIC GELS AND MEDICAL ELECTRODE ASSEMBLIES MANUFACTURED THEREFROM

TABLE OF CONTENTS

Introduction
Background of the Invention
Summary of the Invention
Detailed Description
  Extrudable Viscous Aqueous Polymeric Mixtures
  Preparation of Highly Conductive Non-Stringy Adhesive Hydrophilic Gels
  Test Methods
  General Characteristics of Hydrogel Interfacing Member
    Biocompatibility
    Specific Ion Control
    Hydrophilic Characteristics
    Non-Stringy Adhesive Properties
    Electrical Characteristics
    Physical Properties
  Representative Uses
    Tens
    ESU
    ERG (ECG)
    Defibrillation
    Bio-Feedback
    Conductive Wound Dressings and Their Use in Electrical Wound Healing
Examples
  Example 1
  Example 2
  Example 3
  Example 4

INTRODUCTION

The present invention relates to highly conductive cohesive hydrophilic gels which are also characterized as being substantially non-stringy, more comfortable to use, and more acceptable to the average user. The present invention provides, in particular, extrudable viscous aqueous mixtures comprising poly(vinyl pyrrolidone), a viscosity-enhancing hydrophilic polymer, and an electrolyte which may be crosslinked by exposure to a sufficient amount of radiant energy to form the materials of particular interest.

BACKGROUND OF THE INVENTION

This invention relates to highly conductive non-stringy adhesive hydrophilic gels and medical electrode assemblies adapted for application adhesively to the skin to provide electrical contact therewith.

Medical electrodes comprising, as a conductive member interfacing with the skin of a patient, a sheet or film of a hydrophilic gel are well known in the art. Hydrogel sheets adapted for use in medical electrode-related applications are commercially produced by Promeon, a Division of Medtronic, Inc. (Brooklyn Center, Minn.); Valley-labs, Inc., a Division of Pfizer (Boulder, Colo.) Biostim, Inc. (Princeton, N.J.); Lectec Corp. (Eden Prairie, Minn.); and Conmed (Utica, N.M.).

Numerous U.S. patents disclose hydrophilic gels and medical electrodes employing them. The following illustrate the early state of the prior art.

U.S. Pat. No. 3,357,930 (electrically conductive transparent films comprising a polymeric matrix in gel form, a plasticizer therefor, an ionized electrolyte soluble in the plasticizer, and an ionizable solvent, e.g., solid polyvinyl alcohol, glycerine, lithium chloride and silica).

U.S. Pat. No. 3,911,906 (electrode with skin interfacing film of a pressure sensitive adhesive containing fine electrically conductive particles, e.g., an acrylic copolymer containing carbon powder).

U.S. Pat. No. 3,993,049 (electrode comprising a pliant patch of a formaminated material covered on the side adapted to be placed on the skin with a salt-containing adhesive).

U.S. Pat. No. 3,994,302 (stimulating electrode in which the skin contacting element is an ion-exchange material, e.g., a vinyl pyridine grafted to a polyethylene base).

U.S. Pat. No. 3,998,215 claims an electrically conductive pad which employs a hydrogel impregnated with a fibrous carrier. The polymers disclosed herein as operable require a chemical cross-linking agent. The commercial version thereof sold by the patentee (Minnesota Mining and Manufacturing Co.) has poor skin adhesion and contains bubbles (the latter presumably due to the viscosity of the starting gel and/or the technique employed to impregnate the fibrous carrier with the starting polymer solution). Bubbles in the conductive pad are undesirable because they create local areas of altered electrical properties.

Since the issuance of U.S. Pat. No. 3,998,215, numerous other patents employing a hydrophilic gel as an electrically conducting means which interfaces with the skin of the patient have issued. The following are illustrative of such patents.

U.S. Pat. No. 4,008,721 (tape electrode comprising a skin-contacting layer of adhesive material, e.g., acrylic copolymer).

U.S. Pat. No. 4,054,714 (electrically conductive adhesive useful for binding together surfaces of electronic devices, comprising a polymeric binder, conductive particles whose surfaces are a noble metal and a normally liquid polyhydric alcohol).

U.S. Pat. No. 4,067,342 (tape electrode for transmission of electrical signals into the body through the skin employing a tape having a surface of a conductive material combined with an adhesive e.g., acrylic polymer adhesive, and a second surface with the conductive material comprising a magnetic substance.)

U.S. Pat. No. 4,094,822 (electrode having a cup, which is taped to the skin, containing a semi-solid adhesive polymeric material, e.g., a mixture of polyvinyl alcohol, boric acid, CMC, glycerol and water and an electrolyte, e.g., AgCl or a zinc salt).

U.S. Pat. No. 4,066,078 (electrode with a skin interfacing film having adhesive, plastic and hydrophilic properties, e.g., produced from an interpolymer comprising (a) 10–90 parts of an ester of an $\alpha$, $\beta$-olefinically unsaturated carboxylic acid and a mono- or polyhydric alcohol; (b) 90–10 parts of an $\alpha$, $\beta$-olefinically unsaturated comonomer; and (c) at least 0.02 parts of a cross-linking agent comprising a difunctional monomer.)

U.S. Pat. No. 4,092,985 (disposable electrode comprising an elastically stretchable layer of water permeable porous webbing permeated with a high water content liquid or semi-solid conductive medium).

U.S. Pat. No. 4,109,648 (electrode assembly comprising a self-supporting body of hydrogel, e.g., hydroxyethyl methacrylate polymerized with ammonium per-sulfate and sodium metabisulphite around graphite fiber).

U.S. Pat. No. 4,125,110; Re. 31,454 (electrode comprising as a skin interfacing substrate, a colloidal dispersion of a naturally occurring hydrophilic polysaccharide such as karaya, and a salt in an alcohol as a continuous phase).

U.S. Pat. No. 4,141,366 (electrode for transmitting electrical signals through the skin employing a normally "dry" adhesive which is activated at the time of application by a suitable solvent).

U.S. Pat. No. 4,273,135 (an essentially dry electrode employing as the conductive interface a cohesive, conformable, nonionic hydrophilic synthetic polymer plasticized with a monomer, e.g., glycerol. The electrode is applied to abraded skin wet with normal saline solution or water). This patent contains a detailed description of prior art electrodes in addition to those described and claimed (herein).

U.S. Pat. No. 4,274,420 (an electrode similar to U.S. Pat. No. 4,125,110 in which the adhesive substrate comprises a karaya gum matrix supporting an electrically conductive fluid).

U.S. Pat. No. 4,300,575 (an electrode with a conductive element composed of karaya, carbon black, isopropyl alcohol and karaya gum conductive solution).

U.S. Pat. Nos. 4,317,278; 4,318,746 and 4,362,165 electrodes comprising an annulus of foam with an electrode gel in the central region of the annulus, which gel is the subject of U.S. Pat. No. 4,318,746 and is composed of two polymers, one of which is hot water soluble, e.g., kappa carrageenan, and the other is not, e.g., hydroxypropylmethylcellulose, and which contains a potassium salt to enhance the gel's conductivity.

U.S. Pat. Nos. 4,365,634; 4,393,584; and 4,522,211 (electrodes with adhesive layer secured to a semi-flexible plastic-like sheet, and formed from a known electrically conductive adhesive, e.g., Johnson & Johnson Co.'s "Bioadhesive", disclosed in U.S. Pat. No. 4,066,078, or in U.S. Pat. Nos. 4,008,721; 3,998,215; 3,993,049; and 3,911,906; preferably a hydrophilic material disclosed in U.S. Pat. Nos. 3,822,238, 4,156,066 and 4,156,067).

U.S. Pat. No. 4,383,529 (iontophoretic electrode device with a semi-solid hydrophilic hydrated gel formed, e.g., from agar, a protein or a synthetic polymer, e.g., methyl cellulose).

U.S. Pat. No. 4,458,696 (TENS electrode with an extensible inter facing layer of up to 10 mils thickeners comprised of a carrier portion coated with an electrically conductive adhesive, preferably a 75:25 butyl acrylate-acrylic acid copolymer neutralized with methyl diethanolamine to which are added a water-soluble plasticizer and tackifier, as described in U.S. Pat. No. 3,065,770).

U.S. Pat. No. 4,515,162 (electrode pad comprising a tacky crosslinked hydrogel adhered to an electrode terminal plate, e.g., a polyacrylic acid and a polyacrylic acid salt, water, and a compound containing at least two epoxy groups, as cross-linking component, and optionally a tackifier, e.g., glycerine, propylene glycol or polyethylene glycol, an electrolyte material, e.g., sodium chloride or potassium chloride, a pH controlling agent, a flexibility imparting agent, an antifungal agent, and the like).

U.S. Pat. No. 4,524,087 (electrode with a conductive adhesive thereon which is swellable, dermally-nonirritating conformable, coadhesive, ionic hydrophilic polymer, e.g., produced by UV polymerizing a mixture consisting of triethyleneglycol-bis-methacrylate dissolved in acrylate acid to which is added glycerol and potassium hydroxide in water, using a free radical initiator to initiate polymerization, e.g., a photoinitiator).

U.S. Pat. No. 4,543,958 (electrodes with conductive adhesive film comprising a naturally occurring karaya gum, e.g., available in sheet form from Lectec Corp. or as described in U.S. Pat. Nos. 3,357,930; 3,993,049; 4,066,078; and 4,141,366).

Furthermore, hydrophilic gels are crosslinked polyethylene oxide polymers described in U.S. Pat. Nos.3,264,202; 3,419,006; 3,898,143; 3,993,551; 3,993,552; 3,993,553 and 3,900,378. These references do not disclose hydrogels with the unique characteristics of the present invention.

U.S. Pat. Nos. 4,750,482 and 4,699,146, both issued to Sieverding, describe irradiated poly(vinyl pyrrolidone) formulations to yield hydrophilic elastomeric adhesives. The conductive formulations contain low molecular weight (300–600 MW) polyethylene glycols as plasticizers for the adhesives and require high doses of irradiation to achieve preferred results. The non-stringy characteristic of the present invention is not disclosed.

U.S. Pat. Nos. 4,684,558 and 4,706,680, both issued to Keusch et al., describe tacky adhesive poly(ethylene oxide) gels which may be formulated to also be conductive. The hydrophilic PEO solutions are crosslinked by irradiation. These references also disclose the utility of polyvinyl pyrrolidone as the crosslinked polymer and include an example of PVP (MW=360,000) in a conductive formulation. Like the Sieverding references, cited above, these patents do not disclose or teach the desirable characteristics possible in the present invention.

U.S. Pat. No. 4,593,053, issued to Jevne et al., describe hydrophilic gel compositions including those comprises of PVP and poly(vinyl alcohol). Chemical crosslinking agents are used, however. Likewise, U.S. Pat. No. 4,192,827, issued to Mueller et al., describes hydrophilic gels which utilize relatively exotic comonomers or copolymers which are not indicatively crosslinked.

Although there exists many examples of conductive hydrophilic gels, none embody the unique combination of properties disclosed herein. In particular, previous gels may have had tacky, adhesive, cohesive, or sticky characteristics useful in self-adhesive applications. These hydrogels, when applied to the skin of a human subject, can be extremely sticky and gluey such that most individuals compare the sensation associated with their use with coming into contact with a freshly used piece of chewing gum. This sensation is particularly evident and uncomfortable when removing the previous adhesive gels from the skin and tendril-like strings remain tenaciously adhered to the skin before the hydrogel separates completely. Consequently, a self-adhesive highly conductive hydrogel which is substantially non-stringy and more comfortable to use would be of significant utility.

SUMMARY OF THE INVENTION

The present invention provides hydrophilic gels which are highly conductive and which are useful for a wide range of applications. The highly conductive hydrophilic gels of the instant invention possess other important characteristics which make these hydrogels especially useful in applications in which these materials are brought into contact with the skin of a mammalian subject. In particular, the hydrophilic gels of the present invention are sufficiently cohesive such that substantially no residue remains on the subject's skin after removal of the hydrogel. Of special significance, the instant hydrogels are also sufficiently adhesive and possess a sufficient degree of tackiness such that they do not tend to slide off the subject's skin, though the skin be moist, but these hydrogels are, in addition, substantially non-stringy so that the subject does not associate the use of these hydrogels with an objectionable sticky, stringy sensation akin to handling freshly masticated chewing gum. Furthermore, the present hydrogels are also "non-aggressive," causing no damage to the skin tissue or hair of the subject. Thus, the highly conductive non-stringy adhesive hydrophilic gels of the present invention are particularly well-suited for use in adhesive electrode assemblies meant to be more comfortable and much more acceptable to the consumer.

Accordingly, the present invention provides a highly conductive non-stringy adhesive hydrophilic gel comprising a cohesive homogeneous aqueous mixture of poly(vinyl pyrrolidone) (PVP), a viscosity-enhancing hydrophilic polymer other than PVP having a weight average molecular weight in excess of about 100 kilodaltons (kD), and an amount of a water-soluble electrolyte effective to reduce the transverse electrical resistance of the aqueous mixture to an impedance at 10–60 Hz of less than about 1,000 ohms, preferably less than about 100 ohms. The unique hydrogel of the present invention is produced by an irradiation crosslinking process in which the aqueous mixture of PVP, viscosity-enhancer, and water-soluble electrolyte is exposed to a dose of radiant energy effective to crosslink the macromolecules which are present to a degree which provides a tacky adhesive yet non-stringy hydrophilic gel.

In addition to the elements enumerated above, the present hydrogel may further comprise a variety of chemical and biological additives, as well as other structural components such as supportive scrims or liners.

Aside from providing a highly conductive non-stringy adhesive hydrophilic gel, another object of the present invention is to provide an extrudable highly conductive composition which may be readily processed using conventional mixing, pumping, coating, extruding, or conveying equipment. The extrudable highly conductive aqueous compositions of the present invention make possible a manufacturing process which allows great flexibility in the type of conventional equipment used, in the configuration of the production components, and in the scheduling or rate at which the end product is manufactured. What results is a production process which is manageable, economical, efficient, and most convenient in comparison to a process which would need to be devised for a non-extrudable or poorly extrudable conductive hydrogel precursor. For instance, processes utilizing mixtures which have to be poured into individual trays would necessitate a less flexible more error prone set-up, not easily amenable to interruptions. By contrast, methods which exploit compositions which may be continuously extruded and irradiated on an ordinary conveyor belt, are much more desirable, having greater flexibility as mentioned above.

It is, therefore, another object of the present invention to provide a process for producing a highly conductive non-stringy adhesive hydrophilic gel which comprises preparing a homogeneous aqueous mixture of poly(vinyl pyrrolidone), a viscosity-enhancing hydrophilic polymer having a weight average molecular weight in excess of about 100 kD, and an effective amount of a water-soluble electrolyte to produce an extrudable highly conductive composition; extruding the composition onto a movable surface; and exposing the composition to a dose of radiant energy effective to provide a highly conductive tacky yet non-stringy adhesive hydrophilic gel.

In an article of manufacture aspect, this invention also relates to a medical electrode adapted for providing electrical contact with a patient's skin and comprising:

(a) a conductive member including means for connecting the medical electrode to an external electrical apparatus; and (b) interfacing means comprising a solid sheet of a highly conductive non-stringy adhesive hydrophilic gel, connected electrically with the conductive member, for interfacing electrically with and adhesively to the patient's skin, which sheet is more cohesive than it is adhesive to the patient's skin and is mechanically connected more firmly to the conductive member than it can be adhesively affixed to the patient's skin, thereby enabling concurrent removal of the conductive member and the sheet from the skin after use without leaving a noticeable residue on the skin, wherein such use of said adhesive sheet is less objectionable to the patient because of the substantially non-stringy properties of said sheet, and wherein the hydrophilic gel comprises a uniform cohesive aqueous mixture, substantially free of unbound water, monomers and crosslinking agents, of:

(i) poly(vinyl pyrrolidone) (PVP);

(ii) a viscosity-enhancing hydrophilic polymer having a weight average molecular weight in excess of about 100 kilodaltons (kD); and (iii) amount dissolved in the water of a water-soluble electrolyte effective to reduce the transverse electrical resistance of said aqueous mixture to impedances at frequencies between about 10 Hz to about 60 Hz of less than 1,000 ohms, which aqueous mixture had been exposed to a dose of radiant energy effective to provide a highly conductive non-stringy adhesive hydrophilic gel.

In a method of use aspect, this invention relates to a method of transmitting an electrical signal from the skin of a patient employing a medical electrode of this invention.

In another method of use aspect, this invention relates to a method of transmitting electrical energy to the skin of a patient employing a medical electrode of this invention.

In a method of manufacture aspect, this invention relates to a method of manufacturing a skin interfacing member of a medical electrode of this invention which comprises subjecting a liquid film of a uniform aqueous mixture, having a viscosity of at least about 8,000 cps, of about 0.1 to about 10 wt % of a water-soluble electrolyte, about 0.5 to about 5 wt % of a viscosity enhancing hydrophilic polymer having a weight average molecular weight in excess of about 100 kD, and about 5 to about 35 wt % of poly(vinyl pyrrolidone) having a weight average molecular weight of about 500 to about 2,000 kD to an amount of high energy radiation effective to convert the liquid film to a sheet of a viscoelastic highly conductive non-stringy adhesive solid and thereafter forming the thus produced film into a skin interfacing member of a medical electrode.

It is therefore an object of the invention to provide medical electrodes employing as a skin interfacing conductive member a hydrophilic gel which comprises water, a crosslinked polymer of poly(vinyl pyrrolidone), a viscosity-enhancing hydrophilic polymer, and an electrolyte.

It is another object of this invention to provide a conductive hydrophilic gel which is non-aggressive and substantially non-stringy to the touch such that its use is less objectionable and more comfortable to the user.

It is another object to provide electrodes which comprise, in part, hydrophilic gels which are biologically inert.

It is another object to provide such electrodes which adhere to the skin when affixed thereto without the necessity of skin pre-preparation, e.g., abrasion or wetting the skin and/or drying with solvent.

It is a further object to provide such electrodes whose adherence to the skin are not adversely affected by the presence of normal amounts of moisture on the skin.

It is a further object to provide such electrodes with superior and stable electrical properties, which are suitable for long term use and which can be peeled off the skin after use without damage to the skin and without having a noticeable residue.

It is a further object to provide such electrodes whose hydrophilic gels are free of leachable ingredients, e.g., monomers, plasticizers, crosslinking agents, tackifiers, etc.

It is a further object to provide such electrodes which do not readily lose its water content upon exposure to ambient atmosphere.

It is a further object of the present invention to provide coatable, extrudable viscous aqueous polymeric mixtures which may be conveniently processed into highly conductive non-stringy adhesive hydrophilic gels.

It is a further object to provide methods for transmitting electrical signals from the skin or electrical energy to the skin employing a medical electrode of this invention.

These and other objects of the present invention will become apparent to those skilled in the art from the descriptions and examples which follow.

DETAILED DESCRIPTION

The hydrophilic gels employed in this invention are unique in that although they are electroconductive, they are substantially free of unbound water. This property is important for several reasons. First, it means that the gel does not "bleed" free water under the influence of pressure and/or elevated temperatures, which bleeding can adversely affect one or both of the gel's non-stringy adhesiveness and/or uniformity of conductivity. Second, it means the gel is not "broken" easily if subjected to temperatures near the freezing point of water. This characteristic is very important from a storage and shipping stability point of view. Finally, the gel's resistance against "bleeding" free water renders it more resistant to "drying out" after being removed from its sealed gas and moisture impermeable package.

Because some medical electrodes need to be sterile, the packaging of the electrode should be adaptable to ensure such sterility. Although this process cannot conveniently be achieved conventionally by autoclaving, because heating the electrode to extreme temperatures could adversely affect the polymer or alter the moisture content of the gel, sterility can readily be accomplished by other means, e.g., by treatment with ethylene oxide. Alternatively, the electrode may be packaged and subjected to the high energy radiation step which converts the starting viscous polymer mixture to a solid hydrogel. Such a process effectively and conveniently sterilizes the hydrogel and associated structural and packaging materials.

The hydrogels employed in this invention are characterized by being tacky non-stringy viscoelastic solids which, in the tack rolling ball method (TRBM) test described hereinafter, typically give a rolling ball distance of at least about 15 mm and typically give an adhesion energy force in the Adhesion Energy Density (AED) Determination Test, described hereinafter, of at least about 5 g-cm/cm$^2$. Notably, these hydrogels also possess a swell ration (SR) of at least about 5 and a value for the percent gel of at least about 80. Moreover, these sheets have greater cohesive strength than adhesive strength, whereby the sheet can be removed from a surface to which it is affixed without leaving a visible residue. Because the sheets of the present gels are integral single structures, much like films of thermoplastic polymers, they have excellent cohesive strength which prevents material from separating from the sheets when they are peeled off the subject's skin.

Unlike the conductive adhesive hydrogels of the prior art, however, the present hydrophilic gels are substantially non-stringy such that they may be applied and removed without the objectionable stringy sensation associated with the use of previous tacky gels. These previous materials are so tacky and sticky that tactile examination thereof leaves one with the strong impression that a residue is left on the skin after the gel is removed. Most people find this impression and the accompanying sticky, stringy sensation objectionable, even unacceptable. This extreme characteristic tackiness and stringiness is, therefore, undesirable. Quite surprisingly then, it has been discovered, that cohesive hydrophilic gels which are sufficiently tacky and adhesive and yet substantially non-stringy can be produced. The application and subsequent removal of the present non-stringy adhesive hydrogels are not accompanied by any discomfort or irritation, both physically and in matters of consumer distaste.

It has been discovered further that highly conductive hydrophilic gels may be produced which also embody the desirable characteristics of cohesiveness, adhesiveness, sufficient tackiness, non-aggressiveness, and non-stringiness mentioned above.

The hydrophilic gels are a cohesive uniform mixture of water, an electrolyte, a crosslinked poly(vinyl pyrrolidone) (PVP), and viscosity-enhancing polymer. Not only are these gels substantially or completely free of unbound water, the advantages of which are discussed above, they are substantially free of discrete polymer particles which could settle out or otherwise adversely affect the physical, electrical or chemical properties of the gels. It should be noted that the hydrogel compositions described herein may exist as a multiphase system comprising the high molecular weight macromolecules which are present in the uniform mixture. The irradiative crosslinking process "freezes out" these microphase regions to provide a stable highly useful material. In fact, the materials of the present invention remain substantially unchanged even after a storage period exceeding one year, under ambient conditions and with properly sealed packages. These materials even retain their desirable physicochemical and electrical properties for at least one month at an elevated temperature (e.g., at about 50° C.).

EXTRUDABLE VISCOUS AQUEOUS POLYMERIC MIXTURES

The hydrogels of the present invention are produced by exposing an aqueous mixture of PVP, viscosity-enhancing hydrophilic polymer, and electrolyte to a dose of high energy ionizing radiation effective to form a solid gel-like material It has been found that irradiation of these extrudable viscous aqueous polymeric mixtures produce gels which are highly conductive, cohesive, adhesive, sufficiently tacky, and yet non-stringy.

The PVP is typically a polymer of N-vinyl-2-pyrrolidone having a weight average molecular weight ($M_w$) of about 500 kilodaltons (kD) to about 2,000 kD. An advantageous polymer is PVP having a Mw of about 1,000,000. Homogeneous aqueous mixtures comprising about 5 to about 35 weight percent of PVP are suitable to achieve the objects of the present invention. Preferably, the concentration of the PVP in the aqueous mixtures are about 10 to about 25 weight percent, most preferably 15 to 20 wt %. The irradiation crosslinking of PVP mixtures are most recently described in U.S. Pat. No. 4,699,146 issued to Sieverding, the disclosure of which is incorporated herein by reference.

To reduce the transverse electrical resistance of the homogeneous aqueous mixtures described herein and consequently, the hydrogels which are produced therefrom, a variety of electrolytic substances may be added to the mixtures in amounts sufficient to produce conductive products. These electrolytes may be ionizable inorganic salts, organic compounds, or combinations of both. Examples of such salts include, but are not limited to, ammonium sulfate, monoethanolamine acetate, diethanolamine acetate, sodium lactate, sodium citrate, sodium chloride, magnesium sulfate, calcium sulfate, ammonium acetate, magnesium chloride, magnesium acetate, or combinations thereof. Preferably, the electrolyte used is stable and inert upon dissolving in the aqueous mixture and the subsequent radiation crosslinking step. Preferred salts are potassium chloride, sodium chloride, magnesium sulfate, or magnesium acetate. Potassium chloride is most preferred. Although virtually any amount of electrolyte may be present in the mixture, a breakdown in viscosity is observed as discussed further below, and it is preferable to have an amount of water-soluble electrolyte present at a concentration of about 0.1 to about 10 wt % of the mixture. However, the amount of electrolyte present must be effective to reduce the transverse electrical resistance of the mixture, and the resulting hydrogel, to an impedance at 10-60 Hz of less than about 1,000 ohms. Typically, about 5 wt % of an electrolyte such as potassium chloride, is sufficient to reduce the impedance at 60 Hz to much less than about 100 ohms.

It has been observed that the addition of certain electrolytes, particularly the inorganic salts, to aqueous PVP mixtures results in a breakdown of the viscosity of the initial electrolyte-free PVP mixtures. In general, the initially viscous mixture becomes less viscous to a point that it pours and spreads quite easily. Such a nonviscous mixture is difficult and taxing to work with because films of such materials do not retain their shape until the films are irradiated sufficiently. Specially modified conveyor systems have to be devised to keep such a material from running off any surface on which such a material is held. The configuration, shape, and thickness of the liquid films are thus difficult, if not impossible, to control reproducibly. Significantly, such free-flowing mixtures cannot be extruded successfully with conventional equipment, if at all. Furthermore, a production line, in which such nonviscous mixtures are to be treated, could not conveniently be interrupted even for very short periods of time. Such circumstances may adversely affect the electrical properties of an electrode assembly, as well.

It has thus been discovered that the introduction of a hydrophilic polymer having a weight average molecular weight in excess of about 100 kilodaltons, in as little as a few percent by weight of the total mixture, can enhance the viscosity of the conductive polymeric mixture such that the final viscosity is restored to a degree providing coatable, extrudable viscous aqueous polymeric mixture. Furthermore, when exposed to radiant energy at an effective dose, a film of the extrudable aqueous mixture is transformed into a cohesive gel-like solid having the desirable highly conductive tacky yet non-stringy adhesive properties characteristic of the hydrogels of the present invention.

As stated above, the viscosity-enhancing hydrophilic polymer should have a sufficiently high weight average molecular weight, $M_w$. In general, such a polymer should have a $M_w$ in excess of about 100,000 or 100 kilodaltons (kD). The viscosity-enhancing hydrophilic polymer may have a $M_w$ as high as 10 or 15 million. Such a polymer may be derived from natural, synthetic, or semisynthetic sources; it may be linear, branched, crosslinked, noncrosslinked, water-soluble, or water-insoluble, so long as it is hydrophilic in nature.

Examples of suitable synthetic materials useful as viscosity-enhancers include, but are not limited to, polyacrylamide, poly(vinyl alcohol), a polyacrylate salt, poly(ethylene oxide), poly(ethylene imine), polyacrylamide sulfonic acid or their salts, polyacrylonitrile, hydrophilic derivatives, mixtures, blends, or copolymers thereof. A preferred polymer is poly(ethylene oxide) having a $M_w$ of about 500 to about 2,000 kD, preferably about 900 kD.

Some very useful semisynthetic polymers are the derivatives of cellulose. For example, methylcellulose, ethylcellulose, carboxymethylcellulose, hydroxyethylcellulose, or the like may be used to good advantage. A particularly useful cellulose derivative is a carboxymethycellulose (CMC) having a weight average molecular weight of about 700,000, such as CMC-7HF available commercially from Aqualon Company (Wilmington, Del.).

The addition of such viscosity-enhancers to the aqueous electrolyte PVP mixtures in as little as 1 to 2 wt % of the mixture increases the viscosity to at least about 8,000 cps, preferably 10,000-20,000 cps.

Other suitable macromolecules derived from natural sources include, but are not limited to, starch, agar, dextran, dextrin, carrageenan, xanthan, guar, their derivatives, or mixtures thereof.

Other components may also be present in the highly conductive non-stringy adhesive hydrogels of this invention, if so desired. It is important to keep in mind, however, that one of the advantages of the instant hydrogels is that they can be prepared with all the attendant properties and surface characteristics described herein without the need for extraneous chemical crosslinking agents, monomers, and the like. One should therefore try to minimize the presence of any additive which may be present so that the full benefits of the invention may be realized. In addition, the presence of these additional components may necessitate an adjustment in the dosage of radiant energy applied to the resultant extrudable viscous mixtures to arrive at the non-stringy hydrogels of choice. This adjustment generally requires further exposure of the multicomponent mixtures to high energy radiation. For instance, additives may be uniformly dispersed in the instant aqueous mixtures (and, consequently, the resulting hydrogels), which additives comprise preservatives, stabilizers, fire retardants, pigments, refractive particles, antifungal agents, bacteriacides, antibiotics (e.g., silver sulfadiazine), cosmetics (e.g., glycerine, urea, allentoin, sulfur, antraquinone, hydroquinones), moisturizers, pharmaceuticals, anesthetics (e.g., benzocaine), anti-microbials (e.g., mercurochrome, povidine iodine, iodine), healing agents (e.g., collagen), and the like. These additives may be present in individual or total amounts of about 0.001 to about 3 weight percent of the total mixture, preferably not exceeding about 3 weight percent in the final product.

Specific examples of preservatives or "biocides" include, but are not limited to, Dowicil- ®, methyl paraben, ethyl paraben, propyl paraben, butyl paraben, paraben salts, Cosmicil ®, glydent, germall, or combinations thereof. Other formulations for use in topical applications may further comprise boric acid, Burrows solution, and the like.

PREPARATION OF HIGHLY CONDUCTIVE NON-STRINGY ADHESIVE HYDROPHILIC GELS

A hydrogel conductive sheet suitable for use in a medical electrode of this invention can be produced by mixing the water soluble poly(vinyl pyrrolidone) with the selected electrolyte and water to form an aqueous mixture. The viscosity-enhancing hydrophilic polymer may then be added to give the extrudable viscous feed. Alternatively, particularly with CMC as the viscosity-enhancer, one slowly blends the dry polymer into an aqueous mixture of the electrolyte, viscosity-enhancer, and additive, either at ambient or elevated temperatures. Preferably, the viscosity-enhancing hydrophilic polymer is added to a sufficient quantity of water to provide a viscous solution. To this solution is added sequentially the major matrix polymer followed by the electrolyte. Alternatively, a hot solution of the polymer can be prepared and a concentrated solution or mixture of the selected salt viscosity-enhancer and additive slowly blended therewith to achieve the desired or final concentration of desired components. The viscous liquid feed is then extruded, preferably onto a flat surface to form a liquid film thereon, e.g., a film of PVP or a PVP coated sheet of polyethylene. To contribute to the strength of the hydrogel both in tension and flexure a low area-weight scrim can be incorporated during fabrication before crosslinking The scrim which is in intimate contact with the hydrogel can be of mesh type geometry, either woven or non-woven, e.g., non-woven monofilaments heat sealed together at their interstices or a sheet of thermoplastic polymer with holes in a geometric pattern heat-stamped therein, provided the scrim in is of substantial open area and low area weight, e.g., from about 0.1 to 5 mil in thickness and an area weight of about 0.002 to 0.2, preferably about 0.003 to 0.1 g/inch$^2$. Preferably, the scrim and the hydrogel material are present in a range of thickness of about 0.25 to about 2.5 mm. The scrim is preferably fabricated from a natural or synthetic hydrophobic polymer, e.g., a polyethylene, polypropylene, polyester, polyamide homopolymer. These materials are preferably non-plasticized water-insoluble polymers so that they cannot leak impurities into the hydrogel.

The resulting liquid film is then subjected to a dose of high energy radiation sufficient to convert said film into a non-stringy adhesive solid gel. To facilitate production, the liquid film is preferably backed on one or both sides with a thin peelable hydrophilic sheet, e.g., polyethylene or plastic coated release paper, before it is irradiated. Either or both plastic sheets are then peelably removable after formation of the hydrogel sheet, either before packaging or before use. The hydrogel sheet, which is now a viscoelastic solid, can be cut to desired size and shape for use as the conductive element that contacts the skin in a fabricated electrode device. Depending upon the application, different types of backing sheets can be used on one or both sides of the hydrogel sheet, e.g., a non-peelable sheet can be used on one side only or a peelable sheet on one side and a non-peelable sheet on the other.

The poly(vinyl pyrrolidone) formulations useful in these applications include those incorporating and binding high concentrations of water while maintaining adequate surface tack (adhesiveness), sufficient strength (cohesiveness), and substantial non-stringiness. The polymer/salt/viscosity-enhancer/water mixture should be viscous enough to be extrudable and to form into a sheet-like configuration, e.g., a liquid film of about 0.1 to 2 mm thickness, before crosslinking Preferably, the viscosity of the aqueous mixtures exceeds about 8,000 cps. If a scrim is incorporated into the body of the mixture, the mixture should project beyond both faces of the scrim and all surfaces of the scrim should be wet with the solution. This casting technique is possible with conventional equipment and can be continuous, thereby forming an elongate continuous sheet or film, or discontinuous, i.e., applying individual segments of the mixture of a size and shape corresponding to single electrodes. Any quantity of the extrudable viscous aqueous mixture may be applied to a backing film to form a sheet of hydrophilic gel capable of yielding a plurality of individual interfacing means for individual electrodes, or a large single sheet which can be cut up to form a plurality of interfacing means. The sheets may also be cut into long strips and rolled into rolls as a tape. The thickness of the aqueous film mixture that is applied to the backing sheet generally is dictated by the viscosity of the solution and whether or not a scrim is incorporated therein.

After the viscous mixture is applied or cast to the desired thickness, it is then subjected to crosslinking high energy irradiation, such as a high energy electron flux as produced by an electron accelerator or Van De Graaf generator. In general, alpha particles, beta particles, gamma rays, X-rays, electron beams, or high energy ultraviolet radiation may be used effectively to initiate or precipitate the crosslinking of polymer chains. The major requirement is that the beam of electrons be of sufficient energy to completely penetrate the mixture, so that the mixture receives a radiation dose effective to crosslink the entire cross section of the sample. Proper dose/energy/thickness relationships are readily available to those skilled in the art of radiation processing and therefore need not be discussed in detail. To achieve the desired degree of uniform crosslinking, i.e., effective to convert the viscous polymer/viscosity-enhancer/salt/water mixture into a viscoelastic nonstringy adhesive gel-like solid, doses typically of about 0.5 Mrads to about 4 Mrads, and usually about 0.5 to about 2 Mrads are required, depending upon the selected polymer, its concentration, viscosity-enhancer and its concentration, the selected salt and its concentration and the presence or absence of selected functional, therapeutic agents, or other additives. Most preferably, these formulations are indicated at a dose of about 0.7 to about 1.8 Mrad.

In one specific embodiment of the present invention, a conductive non-stringy adhesive hydrogel is produced from an aqueous mixture comprising 20 wt % PVP, 1 wt % PEO (as the viscosity enhancer), 5 wt % potassium chloride, 0.1 wt % Dowicil-200, 0.02 wt % propylparaben, 0.15 wt % methylparaben, 0.02 wt % ethylparaben, and 0.007 wt % butylparaben. The extrudable viscous aqueous mixture may be irradiated under a variety of dosage conditions (See, Examples Section). In yet another specific embodiment of the present invention an aqueous mixture comprising PVP (15 wt %), CMC (1.5 wt %), KCl (5 wt %), Dowicil-200 (0.1 wt %), methylparaben (0.15 wt %), and propylparaben (0.03 wt %), is also irradiated under several dosage conditions, as described in the Examples Section to provide useful hydrogels according to the present invention. The physical properties of the resulting hydrogels are disclosed in Table I including the AED and TRBM values, SR, and % gel. The corresponding electrical data on two hydrogels in particular are presented in Table III. Most preferably, the hydrogels of the instant invention have AED values of at least about 7 g-cm/cm$^2$, TRBM values of at least about 15 mm, swell ratios of at least about 5, and percent gels of at least about 80. After the conductive hydrogel sheet is irradiated and converted into a viscoelastic solid, it can then be incorporated into an electrode. First it is cut to size, if it is not formed in its desired final shape. If both faces of the hydrogel are covered with backing material, one of its faces is freed from the backing material. The side freed from the backing material is then affixed to a non-porous support conductive member, e.g., a material which contains a conductive metal button, snap, or tab of conductive foil-polymer laminate which is capable of receiving an electrode lead wire and connector to an external electrical apparatus. The electrode is then ready to be packaged. The final package preferably is a gas, moisture and microorganism impermeable sealed pouch or envelope, e.g., formed by heat sealing a heat sealable aluminum foil polymer laminate.

When a packaged electrode is ready for use, it is removed from its package, the remaining backing material is released by peeling it from the gel interfacing sheet, and it is applied to the skin of the patient. The electrode lead wire is then attached to the electrode at the fastener conductive member. Alternatively, the lead wire can be attached to the electrode before the remaining backing material is removed, the backing material then removed and the electrode with the connecting wire attached applied to the skin. Alternatively, the packaged electrode can be provided with its own electrode lead wire already attached. The same sequence of backing material removal and application of the electrode to the skin would then apply without the necessity of attaching a lead wire to the electrode before or during application.

The hydrogel interfacing member of the electrodes of this invention have high adhesive strengths, which means that they can readily be affixed to the skin and will adhere thereto with little risk of accidentally dropping off through loss of adhesion. At the same time, the hydrogel interfacing member is substantially non-stringy and is, therefore, more comfortable and more readily acceptable to the user. Because the interfacing member is water based, it is relatively immune to the effects of moisture on the skin and will not slide off as a result of perspiration forming under the electrode while affixed to the skin. They also have high cohesive strengths, which means that they can be removed from the skin after use without leaving any visible residue. Interestingly, although the gels have a high adhesive strength, it is not high enough to pull hairs from the skin or irritate the skin when the gel is removed therefrom. Furthermore, the use of the present gels is not associated with any objectionable sensation.

The medical electrodes of this invention containing a sheet of a PVP/viscosity-enhancer/electrolyte hydrophilic solid gel, as disclosed herein as a skin interfacing member, can assume a wide variety of shapes and construction, which are within the knowledge and skill of the practitioner in the art.

Because the hydrogels will lose water eventually under ambient conditions, they are preferably stored in a water and gas impermeable container, e.g., a polyfoil packet formed from the laminated plastic conventionally used to store measured amounts of freeze-dried or ground coffee. Sealed envelopes are conventionally produced by heat sealing a pair of sheets of thin plastic around the hydrogel sheet-backing laminate, or medical electrode in which a hydrogel sheet is mounted, or by heat sealing the open end of an otherwise sealed packet or envelope formed from a single sheet of the laminate.

If the film or sheet of instant PVP hydrogel is to be stored separate from the components of the medical electrode with which it is to be used, both faces thereof are preferably covered with a sheet of peelable release liner, e.g., polyethylene. If the sheet of hydrogel is to be stored mounted in the medical electrode with which it is to be used, its exposed face, i.e., the face to be applied to the skin, is covered with such a release liner. If both faces are covered with a release liner, optionally different liners can be employed, one of which is more readily removable therefrom than the other, e.g., a sheet of polyethylene covering one face and a sheet of "Mylar" plastic covering the other, thereby ensuring that a predetermined face of the film or sheet is exposed first. In some end use applications, one of the faces of the film or sheet is covered with a conductive liner which is not removable and is used as a conductive member in the final electrode assembly. Other variations should be evident to the skilled practitioner.

The present hydrogel sheet or film can be packaged singly or in multiples between the release liner or liners. In TENS end uses, it is desirable to mount a plurality of spaced apart circles, squares or rectangles of the film or sheet of the hydrogel on a plastic sheet, e.g., a 2 mil film of "Mylar" plastic and cover their exposed face with a different release liner, e.g., a 2 mil film of polyethylene or a sheet of polyethylene coated paper release liner. Either or both of the facing films can be appropriately scored to facilitate removal of the units of PVP hydrogel sequentially. If desired, one face of a plurality of units of the hydrogel can be covered with a large backing sheet, one facing film which is unscored and the other face covered with a release liner of the same dimensions as the units of the hydrogel so that a unit of the hydrogel and the latter release liner can be peeled off together, one at a time from the large backing sheet.

In another embodiment, a large sheet of a laminate formed from the PVP hydrogel and films of plastic covering its faces, e.g., a film of polyethylene on one face and a film of Mylar on the other, is scored at spaced intervals in both directions thereby producing a plurality of severable square or rectangular units of the laminate, each for use individually in conjunction with a medical electrode by tearing the laminate along a pair of perpendicularly positioned lines, thereby releasing a unit of the laminate from the sheet.

When the sheet of conductive PVP hydrogel is of the same dimension as a release liner covering an exposed face thereof, removal of the latter is facilitated if the latter is slit into pieces, thus providing an edge which can be easily raised with a fingernail or tool.

If desired, a plurality of circles, squares or rectangles of the hydrogel with a release liner covering one face can be "stacked" one upon the other so that a column of such units of the hydrogel sheet with both faces covered with a release liner is formed. Desirably, in such an arrangement, one side of the release liner has a higher adhesive value than the other, so that only one unit of the hydrogel is removed at a time from the column. Such columns can be conveniently stored in glass jars or aluminum lined paper tube with a moisture impervious cap which form a gas and moisture impervious sealed container.

TEST METHODS

As stated above, the hydrogels employed in this invention are characterized by high conductivity, surface adhesiveness, sufficient cohesiveness to maintain structural integrity when being removed from the skin, while being substantially non-stringy.

The manner in which hydrogel film of this invention adheres to the skin is an important aspect of this invention. The hydrogel adheres sufficiently to both dry, damp, clean, or soiled skin. It is tolerant to perspiration which forms from the skin under the hydrogel after the electrode is applied to the skin, because the hydrogel can adsorb a substantial amount of water before it loses its surface tack. Conversely, because it is 65+% water, it does not create chemical bonds with the skin and hair which results in pain and/or skin damage when an electrode employing a conventional adhesive-based skin interfacing member is removed after use, and, because it is substantially non-stringy, the present hydrogel is much more comfortable in its use and is less objectionable, less sticky to the touch.

To test for skin adhesiveness, samples of the hydrogel with backing removed from one side can be applied to the skin and left on. This step is done both with the scrim-containing hydrogel films alone and with a scrim-containing hydrogel film attached to a support backing bearing a metal conductive snap electrical terminal. How well the hydrogel adhered to the skin is then observed and how easily the electrode material can be separated from the skin is noted, along with whether or not any residue is left on the skin.

The adhesiveness and tackiness of the conductive hydrogel sheet or films can be quantified by the "Tack Rolling Ball Method" (TRBM) as specified by the Pressure Sensitive Tape Council. This test method for adhesive materials is detailed in The American Society for Testing Materials, Designation D3121-73 (Re-approved 1979) which test method is under the jurisdiction of ASTM Committee D-14 on Adhesives. The test utilizes an inclined trough which can be obtained through the Pressure Sensitive Tape Council, 1201 Waakegan Road, Glenview, Ill. 60025, that is equipped with a release lever at the top through which a 16.5 mm diameter, 21.7 g steel ball is released onto the trough. The ball gains momentum as it descends the incline and rolls onto the adhesive surface whose adhesiveness is being measured, the shorter distance the ball travels thereon, the higher the adhesion value.

The test is performed as follows: Remove the backing materials from both sides of a hydrogel sample cut one inch wide and at least three inches long. The test is run in a controlled environment (72° F.±5° F. and 50%±10% relative humidity). A hard, horizontal surface of sufficient size to conduct the test is selected. Both metal and glass plates have proved satisfactory. Before testing each adhesive sheet, clean the inclined trough thoroughly with isopropanol.

The specimen to be tested is placed flat, adhesive side up, in line with the inclined trough. The end of the specimen opposite the incline is held to the table. Only one test is run on each specimen. Each time before the ball is rolled onto the hydrogel, it is thoroughly cleaned with distilled water, isopropanol, or another appropriate solvent, which removes any residue that might otherwise remain from a previous test, and then wiped with a lint-free, bleached, absorbent material to remove any remaining residue. After cleaning the ball or raceway is not touched. Use clean, dry tongs to place the ball on the upper side of the release. Release the ball and it will roll to a stop on the adhesive material. Measure the distance from the point where the ball initially contacts the adhesive to where the ball stops. The average of the stopping distance measurements of five or more tests is recorded. Pertinent additional comments based on visual inspection such as noticeable residue on ball, lift of adhesive from substrate, etc., are noted.

In this test, the hydrophilic gels employed in the electrodes of this invention have tack rolling ball distances of at least about 10 mm, preferably at least about 15 mm. The preferred gels have distances of less than about 60 mm.

Another test that quantitatively measures the extent of crosslinking in a polymeric mixture involves an extraction test. This test provides % gel values and is carried out substantially as described below. A two inch by two inch price of PVP gel and weighing about 2.5 grams is extracted with 200 mL of distilled water for 72 hours at ambient temperature. The excess water is then removed from the swollen sheet which is then weighed (See, the swell ratio, infra). The swollen sheet is then baked in a 50° C. oven for 24 hours. The resulting desiccated gel is then weighed. The ratio of the "dried" gel weight over the original weight of the polymer in the sample is the gel fraction or % gel. Preferred hydrogels of the present invention have % gel values of at least about 80 percent.

Another important feature for an adhesive sheet especially one that is intended for utilization in wound management applications is its absorptive capacity. This property is important because an adhesive on the skin can readily lose its adhesive bond due to a layer of perspiration accumulating at the interface. Moreover, if an adhesive material is utilized as a wound dressing it must be capable of absorbing the exudate from the wound, as this is one of its primary functions. If the gel cannot do so, it will also lose its adhesive bond and move from the site where it was intended to function. For these reasons it is very important for the adhesive sheet to have good equilibrium or absorption capacity for aqueous liquids. A test method that quantitatively measures the absorption capacity of a crosslinked polymer system is the swelling test.

The test method proceeds in exactly the same manner as the extraction test previously mentioned, up to the point of extraction. The weight of the extracted sheet, with unbound excess water removed from the surface, divided by the weight of the original sheet is the swell ratio (SR). In the hydrogels of the present invention, it has been discovered that the preferred embodiments which are highly conductive and adhesive and yet substantially non-stringy are those which have an absorptive capacity, as measured by the swell ratio (SR), of at least about 5.

Another test to measure relative strength and stickiness of an adhesive bond is the Adhesion Energy Density Determination test. This test measures how well a hydrogel sheet adheres to a flat surface. The adhesion energy which is measured is the combined strength of the surface bond of hydrogel sheet to the flat surface and the strength of the hydrogel sheet itself (i.e., a combined cohesiveness/adhesiveness test.

A sample of the hydrogel sheet to be tested is placed unbacked on a clean flat stainless steel block. The block in turn is placed on a block of flexible foam which in turn is placed on a test stand. With the setup in place a steel ring is placed on top of the test sample and aligned with the test probe to be used so that the latter will descend therethrough without touching the ring. A cylindrical (1.5 inch diameter) polymethylmethacrylate test probe then descends into the sample at a constant rate to a constant depth. (In the hydrogel films tested, the descent rate is set at 0.5 mm/sec. and the penetration is set at 1.0 mm.) Before the test probe is made to descend it is cleaned with isopropanol or distilled water and dried with a lint-free cloth, to make certain no residual adhesive material is on the face of the probe before the test is begun. All tests are run at 72° F.±5° F. and at a relative humidity of 50%±10% and each test sample is stored at these conditions for at least one hour before the test. When the test probe has made its 1 mm descent into the hydrogel film and begins its return (at a rate of ascent of 0.344 cm/sec), the adhesive sample being tested has adhered to the face of the test probe. From the start of the return of the probe to complete separation of the test sample from the face of the probe, the force on the probe and the corresponding displacement is recorded using a Voland Stevens LFRA Texture Analyzer and Recorder (Voland Corporation, Hawthorne, N.Y.). The area under the force-displacement curve is the adhesion energy. For the 1.5 inch diameter probe used, it is the adhesion energy per 11.4 $cm^2$, which is the adhesion energy density. For the work reported herein, the force was measured in grams and the displacement measured in centimeters so that all adhesion energy densities are reported in g-cm/$cm^2$.

In this test, the hydrophilic gels of this invention display adhesion energy densities of about 5 to about 60 g-cm/$cm^2$. The preferred gels give values of at least about 7 g-cm/$cm^2$ in this test. Also, under the present test, the hydrophilic gels of the present invention exhibit a force, equivalent to the height of the force-displacement curve, of at least about 180 grams. Preferably, the hydrophilic gels of the present invention exert a force on the test probe equivalent to at least about 250 grams, most preferably 400 grams. In addition, the force-displacement curves obtained for the present non-stringy gels are sharp and substantially featureless.

Because the PVP and/or viscosity-enhancer is crosslinked by high energy radiation, the hydrogels of the present invention are free of both residual monomers and chemical crosslinking agents, a very important consideration for devices which are to be affixed to the skin. If desired, and as mentioned previously, the gels optionally can contain preservatives, antifungal agents, a bacteriostat and the like, bearing in mind that unless special steps are taken to incorporate any such agents into the gel after it is formed, e.g., by application of a film of an aqueous solution thereof to one or both faces of the sheet of hydrophilic gel, the materials selected must be able to withstand the irradiation employed to produce the hydrophilic gel. Furthermore, the presence of these additives can change the radiation doses required to give a product with enhanced adhesion, yet non-aggressive, sufficient strength, but yet non-stringy.

Such additives may be included in formulations at levels of about 3% or less The addition of these extra components usually requires a shift, upward in the radiation dose to reach the same level of desired crosslinking. However, shifts to lower levels are not necessarily precluded.

The physical properties of the hydrogels of Examples 1 through 4 (Section 5), according to their Adhesion Energies, Tack Rolling Ball Distances, Swell Ratios, and % Gels, are listed in Table I, below.

TABLE I

| PHYSICAL CHARACTERISTICS OF THE PRESENT HYDROGELS | | | | |
|---|---|---|---|---|
| FORMULATION[a] | Dose (Mrad) | AED/Force (g/cm)/(g) | TRBM[b] (mm) | % Gel | Swell Ratio |
| 20% (by weight) | 0.76 | 28/425 | 19 | ~79 | ~8 |
| PVP, 1% PEO, | 1.04 | 49/533 | 15 | 85 | 7.4 |
| 5% KCl, 0.3% | 1.09 | 49/382 | 21 | 87 | 7.7 |
| Biocide | 1.34 | 21/600 | 26 | 86 | 5.4 |
|  | 1.54 | 32/381 | 24 | 82 | 6.4 |
|  | 1.80 | 28/406 | 27 | 82 | 5.1 |
|  | 2.13 | 22/350 | >27 | 89 | 5.2 |
| 15% PVP, 1.5% CMC, | 1.0 | 10/214 | 32 | 88 | 7.4 |
| 5% KCl, 0.28% | 1.2 | 8/181 | 39 | 86 | 6.3 |
| Biocide | 1.31 | 9/248 | 39 | 86 | 5.8 |
|  | 1.5 | 7/230 | 35 | 87 | 5.6 |

[a]The PVP used in this formulation had a weight average molecular weight ($M_w$) of about 1,000,000. The PEO had a $M_w$ = 900,000 and the CMC a $M_w$ = 700,000. The biocide comprises a number of preservatives (See, Section 5.2).
[b]The rolling ball used in these measurements was 16.5 mm in diameter and weighed 21.7 g.

The electrode assemblies according to this invention are suitable for application to skin in connection with both electrical signal sensing medical electrical apparatus and electrical energy transmitting medical electrical apparatus, i.e., they can be used both as sensing electrodes and as working electrodes. Examples of "sensing" electrodes are those used in electrocardiogram (ECG), electrooculogram (EOG), electrogastrogram (EGG), surface electromyogram (EMG), electrodermal responses (EDR), electroensephalograms (EEG), visual evoked potential (VEP), and auditory evoked responses (AER). Moreover, because the hydrogels employed therein are biologically inert, the assemblies according to this invention are suited to the detection of signals requiring application to or implanted within sensitive areas of the body, such as the cornea in the electroretinograms (ERG), or in body cavities where the materials of conventional assemblies may prove unsatisfactory, such as in the summated electrocochleograms (ECOG) electro-olfactorograms (EOGs) and measuring electrovaginal potentials (EVP).

Examples of "working" electrodes for which the electrode assemblies of this invention can be used are those adapted structurally for Transcutaneous Electrical Nerve Stimulation (TENS), use as a Electro-Surgical Unit (ESU), External Cardiac Pacing (ECP) and for Defibrillation (DEFIB).

The physical, electrical and chemical characteristics of these two general types of electrodes, plus three sub-catagories of the latter type, are set forth in Table II, below.

TABLE II

| Electrode Type | Size (in$^2$) | Thickness (Mils) | H$_2$O Content (%) | Resitance ohms-cm |
|---|---|---|---|---|
| Sensing | 0.25-1.5 | 20-75 | 80-98 | 3,000-10 |
| Working | 0.5-50 | 50-115 | 80-98 | 50,000-1 |
| Defib. | 4.5-25 | " | 90-97 | 5,000-15 |
| ESU | 5.5-50 | " | 80-95 | 50,000-1 |
| ECP | 12.5-25 | " | 80-93 | 3,500-15 |

For a more extensive discussion of the preceding test methods please refer to U.S. Pat. Nos. 4,684,558 and 4,706,680 the complete disclosures of which are incorporated by reference herein.

GENERAL CHARACTERISTICS OF HYDROGEL INTERFACING MEMBER

The following is a summary of the properties of the hydrophilic gels of this invention.

BIOCOMPATIBILITY

The hydrophilic gel is inert and is not metabolized. It has a normal pH of about 7, which is allowed to "float" between 6 and 8. They have a zero irritation index. Because it is produced by irradiation, the gel is virtually microorganism free, with less than about 10 colony-forming units (CFU) per cubic centimeter (the measurable limit).

The hydrogel contains no extraneous or other objectional ingredients. It does not contain extraneous chemicals such as monomers and cross-linking agents, which are present in chemically linked cross-linked gels, or solvents, etc., which are an integral part of formulated adhesives. All ingredients have proven bioacceptability on contact with the skin. Normal exudants flow into the matrix of the gel away from the user's skin. Its hydrophilic properties eliminate the common requirement for abrasive treatment and/or other skin preparation.

The biocompatibility of the instant hydrogels are expected to be quite favorable because all the ingredients used to prepare the hydrogels are, themselves, highly biocompatible.

SPECIFIC ION CONTROL

Experience has shown that specific ion control with even distribution within the conductive matrix is of paramount importance in electrode performance. The precise ion level and dispersion in the process employed to produce the hydrogel lends itself perfectly to the production of a unique family of controlled conductive-adhesive transmission components. Although the polymer matrix theoretically could hamper ion mobility, the volume resistivity of the hydrogel remains low.

HYDROPHILIC CHARACTERISTICS

The hydrogel contains no free water. The water in the hydrogel is an integral part of the gel structure and therefore cannot be separated therefrom by physical means such as pressure. Thus, the crosslinked matrix remains homogeneous under gravity and even at temperatures approaching freezing water. Its imbibing property enables the hydrogel to cleanse the body surface of water soluble exudates and secretions by drawing them up into the gel by osmosis, thus lowering the skin irritation factors commonly associated with other organic polymers. The gel pad has a distinct advantage of conforming itself to the irregularities of human skin, producing a substantially uniform contact. This characteristic is important because poor skin contact can cause electrical noise or current loss, which can change the accuracy of a biopotential recording or the efficacy of an electrical energy treatment. The high water content also precludes the necessity of preparatory skin shavings which some commercial electrodes require.

NON-STRINGY ADHESIVE PROPERTIES

The hydrogels' non-stringy adhesive characteristics are manifested in its ability to conform to minute irregularities on the surface on which it is placed, yet sparing the user the objectionable sensation associated with handling an extremely sticky, stringy composition akin to freshly masticated chewing gum. While having these non-stringy properties, the present gels retain their cohesive properties. These characteristic meet the criteria of a non-stringy adhesive, without the necessity of additional chemicals. The degree of adhesion to a given surface is a function of the degree of irregularity or porosity of the surface. The hydrogels retain their adhesive quality even while absorbing normal perspiration. The viscoelastic properties of the hydrogel within the gel structure allows it to flow into the tiny interstices of the surface to which it is placed, thereby allowing intimate uniform contact between itself and that surface. This type of adhesiveness allows it to adhere to skin without employing additional chemical bonding agents, which permit the hydrogel to be removed from the skin without pain, skin damage or hair pulling and without leaving any residual components of the gel on the skin itself, as the components are permanently bound within the gel structure.

It has been surprisingly discovered, however, that hydrogels having the desirable electrical properties, discussed further below, having the adhesive properties described above, yet having the non-stringy properties also described herein, may be produced with the addition of viscosity-enhancing hydrophilic polymers of a sufficiently high weight average molecular weight.

These benefits are achieved with very little amounts of viscosity enhancers, as little as about half to about one percent of the total mixture, and by careful exposure of the viscous mixture to the requisite amount of high energy radiation.

ELECTRICAL CHARACTERISTICS

The starting materials used to produce the hydrogel can be formulated with a wide range of amounts and types of ionic materials to produce hydrogels having highly desirable electrical characteristics. The uniform distribution of selected ions results in correspondingly reproduceable electrical properties throughout the hydrogel, thereby lending itself to a wide variety of applications based on its conductive and capacitive properties. Furthermore, the predictable volume resistivity of the hydrogel lends itself to many critical medical applications.

Electrolytes that can be used in the hydrogel include most cations, e.g., ammonium, sodium, potassium, lithium, magnesium, calcium, etc., and both simple and complex anions, e.g., chloride, sulfate, carbonates, nitrates, and anions of organic acids, e.g., acetic, citric, adipic, tartaric, lactic, propionic, glutaric and maleic acids, the latter being preferred in electrodes where decorrosion of the metallic connector may be a problem. Magnesium acetate is especially suitable in this respect. The volume resistivity remains constant throughout the gels intended use, allowing virtually zero decay in the conductance of the skin in medical applications, while allowing an upward even flow of skin excretions through the matrix away from the user. This change is uniform throughout the cross sectional area of the gel because of its balanced osmotic hydrophilic properties.

It is also important to note that because the hydrogels of the present invention have impedance values at 10-60 Hz of as low as about 15 ohms, any variations in electrical properties between sheets of hydrogels will be small on an absolute basis for a given standard deviation of impedance values. Such uniformity is very important because one would want the electrical properties of an electrode to be substantially the same as other electrodes which may also be in use on the same subject.

The electrical properties of particular embodiments of the present invention are listed in Table III.

will withstand loss of water with a force of about 20 psi on a single surface, unlike other types of gels which exude water under the influence of gravity. Its high specific heat is another useful property. The hydrogel sheet is structurally unchanged and functional over a wide range of temperatures beyond its use range. The amount of energy required to raise the temperature of the sheet adds a safety margin in many medical applications. It can also be useful in some combination therapy applications involving heat/cold and electrical stimulation.

Because the hydrogel sheet or film is produced with high energy radiation, such as that produced by an electron accelerator, it can be sterile at a sufficient dosage.

Particular advantages realized with electrodes employing the hydrogel are its stable electrical properties, its excellent adhesion to the skin, and its substantially non-stringy texture. A superior medical electrode should not store electrical charge, should have a low solution potential with the skin, and should be of low impedance. The hydrogels employed in the electrodes of this invention have all of these characteristics. The electrodes also adhere firmly to the skin, ordinarily without the necessity of external adhesive support, depending upon the duration of the application. Also, the surfaces of the hydrogel which are exposed to air during use slowly form a dry crust over a period of time, thereby preventing the bulk of the hydrogel film from drying out and acquiring altered electrical conductivity properties. This property is particularly useful for long term applications.

The electrodes of this invention also exhibit further superior properties upon removal after use. Although the electrodes readily adhere to the skin, they can very easily be removed therefrom in a painless manner without damaging the skin, as do conventional commercial adhesive products. Moreover, upon removal, the electrode leaves no visible residue on the skin, as do many liquid gel-based electrodes. In fact, liquid gel electrode materials must be wiped off the skin in a relatively painstaking manner, frequently by application of soap and water. Because these hydrogels are substantially non-stringy, they are particularly more comfortable to use and are more acceptable to the patient. Also, during

TABLE III

| | ELECTRICAL PROPERTIES OF THE PRESENT HYDROGELS | | | | | |
|---|---|---|---|---|---|---|
| FORMULATION | Dose (Mrad) | Z(10) (ohms)[a] | Z(60) (ohms)[b] | V(IO) (mV)[c] | V(5) (mV)[d] | ΔV(15) (mV/sec) |
| 20% (by weight) PVP, 1% PEO, 5% KCl, 0.3% Biocide | 1.34 | 41 | 14.8 | 1.5 | 17.2 | −0.35 |
| 15% PVP, 1.5% CMC, 5% KCl, 0.28% Biocide | 1.31 | 40 | 14.5 | 3.3 | 18.4 | −0.35 |

[a] AC: Impedance at 10 Hz
[b] AC: Impedance at 60 Hz
[c] V(10): Initial resting offset voltage.
[d] V(5): Offset voltage 5 seconds after simulated defibrillation.
[e] ΔV(15): Offset voltage rate of change 15 seconds after simulated defibrillation.

PHYSICAL PROPERTIES

The basic sheet form of the hydrogel has both structural integrity along with resilient memory which permits it to return to and retain its original form when pressure is applied to the X-Y or Z axis. The product application, the hydrogel of the electrodes of this invention does not stain or stick to clothing. All of these advantages are accomplished employing ingredients which have an excellent history of biocompatibility so there is little likelihood of skin eruption or irritation.

Both sensing (detecting electrical signals on the skin) and working (transmitting electrical energy to the skin) electrodes according to this invention have numerous advantages over the prior art versions presently available commercially. Some of these are listed in Table IV below.

TABLE IV

| Property | | Advantage |
|---|---|---|
| 1. Thermal | Working: | Less chance of burns in ESU use. |
| | Sensing: | Less temp. drift in ECG/EEG use. |
| | Both: | Patient friendly; can be warmed to skin temp.; wide range of storage conditions acceptable. |
| 2. Adhesion | Working: | Less chance of radio freq. burns; minimal loss of contact due to detachment in ESU use; adheres to paddle, no chance of a short due to movement in DEFIB. |
| | Sensing: | Less motion artifact in ECG/etc; Less false alarms due to detachment; Can be easily moved or reapplied in operating field. |
| | Both: | No tapes, foams needed. |
| 3. Clarity | Working: | Able to see burns thru ESU, TENS & DEFIB applications. |
| | Sensing: | Can detect local skin reactions. |
| | Both: | User preference, clean look. |
| 4. Impedance | Working: | Able to select medium impedance (by control of salt content) for EGU & DEFIB uses. |
| | Sensing: | Able to select low impedance for ECG/EEG/EMG/etc. applications. |
| 5. Uniform Impedance | Working: | No rf burns due to hot spots in ESU applications. No patient burns due to arcs in DEFIB applications. |
| | Sensing: | Low DC offset due to un-matched ECG electrodes. True signal reproduction in relative EEG/EMG signals. |
| 6. Skin Contact | Working: | Uniform application of power thru skin in chance of a short due to movement DEFIB, ESU, etc. |
| | Sensing: | Less noise in ECG/EEG use. |
| | Both: | Low surface impedance. |
| 7. Self-Sealing | Working: | Less edge effect in ESU use. No shorts due to product migration in DEFIB use. |
| | Sensing: | Low external pressure induced DC offset in ECG/EMG use. |
| | Both: | Can be cut to size. Less water loss in long term use. |
| 8. Conformability | Working: | Less burns at thin, boney sites in ESU use. Less arcs at hairy, thin, boney sites in DEFIB use. Less Air Gaps. |
| | Sensing: | Low motion induced artifact. Stays in place in ECG use. |
| 9. Bioburden | Both: | Very Low. |
| 10. Reuseability | Both: | Can be easily rehydrated a number of times by moistening with water. |

REPRESENTATIVE USES

The following is a description of specific end use applications of the highly conductive hydrophilic nonstringy surfaced viscoelastic solid gels employed in the medical electrodes of this invention and the advantages associated therewith.

TENS

The TENS (Transcutaneous Electrical Nerve Stimulation) electrode coupling media is produced from low to medium ionic concentration, e.g., about 4 to 5 wt % of sodium chloride, hydrogel sheets. It is used as a disposable interface between a "standard" reuseable carbon electrode and the skin. The substance can also be used as an electrolyte in contact with its own carbon electrode material. The inert ingredients preclude skin irritation and the osmotic properties permits exudant to be carried away. The uniform ion control allows uniform current distribution and the hydrophilic properties prevents any air-gaps that can cause alternating current rectification. The excellent adhesive characteristics prevent accidental electrode detachment and the consistent electrical properties assures continuous effective treatment. The cohesive properties allows the hydrogel sheet to be cut to size and easily removed from the skin and electrode, offering true ease of use. This also holds true of the totally disposable product where ease of use and no clean-up are controlling factors. Finally the high specific heat and intimate contact becomes a deterrent to "hot spots" and any thermal burn potentials.

ESU

The ESU (Electro-Surgical Unit) electrode is produced from lower ionic hydrogel sheet, e.g., 6.7 wt % magnesium acetate. The dispersive radio frequency (grounding pad) return electrode application is a perfect conductive/adhesive application. The adhesive safety factor which prevents electrode removal and subsequent RF burns is of paramount importance. The precise ionic distribution and control prevents current pooling and small thermal burns. The hydrophilic properties lessen interference from surgical fluids and assures close physical contact, thereby preventing muscle stimulation from rectified current. The high specific heat provides another safety factor in diminishing edge effect heating and electrolyte drying. In addition, the instant hydrogel is characterized as having an inherently uniform internal composition. As a result, the hydrogel is thermodynamically homogeneous and resists uneven gel or salt distribution during storage. Thus, electrodes manufactured from these hydrophilic gels do not suffer from gel separation or gel migration, ensuring the presence of an adequate and uniform surface area for proper current dispersion from the body. The biological inertness of the hydrogel assures that local skin reactions, which could be confused with possible RF burn, will not be produced. The hydrogel's chemical inertness assures no ingredient breakdown via electrolysis and the hydrogel's excellent response to elevated temperatures also assures performance under adverse use conditions.

EKG (ECG)

The PVP hydrogel-based EKG (electrocardiogram) electrodes have the widest variety of specific use applications, made possible by the ability to produce hydrogels of specific ionic strength. The ion concentration is chosen from a high, e.g., 7–8 wt % potassium chloride, low, e.g., percentage for high performance exercise use to 5–6 wt % potassium chloride, concentrations for long term applications. The ability to use ions that have previously been hard to control allows the production of a near perfect electrode on a consistent basis. The unique ability of the hydrogel to be compressed without any associated signal drift makes it ideal for clinical situations. The bound PVP matrix provides a stable signal sensing electrolyte for consistent recording, regardless of changing skin or temperature conditions. The excellent adhesive properties of the hydrogel provides added safeguards against "lead-loss" alarm conditions and the cohesive component provides the sought after ease of use quality. The excellent skin friendliness makes it a perfect choice for long term contact. The hydrophilic characteristics allows good conduction without the patient discomfort of skin abrasives or shaving. Finally, the excellent response to extreme temperatures makes EKG electrodes based on the PVP hydrogels of this invention a good choice for emergency field applications.

DEFIBRILLATION

The defibrillator pad is produced from a sheet of PVP/PEO/KCl hydrogel. The pad is usually used as a conductive media for the application of large amounts of electricity (voltage & current) and also used as a sensing electrolyte for EKG monitoring thru the same electrodes. The excellent electrical properties allows efficient delivery of the therapeutic charge of electricity without a loss of monitoring capability due to its low DC offset. The bound polymer matrix prevents the product from pooling during storage and the unique thermal properties of the gel makes it the perfect choice for field use of these devices. The adhesive component assures proper paddle contact without the fear of electrode cream running, which allows repeated repositioning or re-application of the paddles while maintaining effective skin contact. The hydrophilic properties of the gel sheet assure uniform skin contact without "pitting" and also eliminates the necessity of any skin preparation. The structural stability of the gel sheet allows greater user pressure upon paddle application without fear of pushing the gel away from the contact area. Finally, the clear glass-like property of the gel sheet allows full view of any trauma related injuries.

BIO-FEEDBACK

The Bio-Feedback electrode is produced from a high concentration ionic gel sheet, e.g., 7-8 wt % KCl. Advantageous characteristics of the hydrogel sheet are its ability to firmly adhere to the patient's skin because of it adhesiveness and its ability to be re-positioned because of the cohesiveness. Its specific even ionic concentration allows it to be used with a wide variety of home and clinical electrodes, and permits immediate signal reception. The hydrophilic properties of the gel sheet allow many possible placement sites without the need for any skin preparation. The bio-compatibility and skin friendliness makes long term use possible. The qualities of this product also find identical applications in the EEG, EMG, ENG and Evoked Potential fields. Specific electrical qualities necessary in all the above uses involve low noise potential and small DC offsets because of the low level signals involved. The gels bioinertness is especially important since these applications are frequently proximate to the eyes and mouth.

CONDUCTIVE WOUND DRESSINGS AND THEIR USE IN ELECTRICAL WOUND HEALING

The variable electrolyte content of the present hydrogels makes them suitable conductive dressings for wounds. In particular, these conductive materials may be used in conjunction with electrical wound healing therapy in which beneficial effects have been observed from the application of electrical impulses to sores or wounds.

Two representative references by Alvarez et al. which describe the treatment of wounds through the application of external currents and the use of polymeric wound dressings, in general, are: *J. Invest. Dermatol.* 1983, 81(2), 144–148 and *J. Am. Acad. Dermatol.* 1985, 12 (Part 2), 409–419, respectively. The complete disclosures of these two references are incorporated herein by reference.

EXAMPLES

EXAMPLE 1

A liquid film (ca. 50 mil) of a mixture of 20 wt % poly(vinyl pyrrolidone) (approximate weight average molecular weight $1 \times 10^6$), 1% poly (ethylene oxide) ($M_w$ 900,000), 5 wt % potassium chloride and about 0.3 wt % of selected biocides in water is cast (coated or extruded) onto a 1 mil film of polyethylene backing material. A polyethylene non-woven scrim (0.016 grams/inch2) area weight is immersed into the viscous solution near its center. The scrim-containing solution is covered with a second sheet of 1 mil polyethylene film backing material, producing a sandwich 52 mil thick. This sandwich, held on a movable conventional conveyor belt, is then passed across the beam of a Van De Graaf generator, where it receives 1.34 Mrads of irradiation. The extrudable viscous aqueous mixture is thus converted to a sheet of a solid viscoelastic hydrogel. A one inch square sheet is cut from the sandwich and the backing materials on both sides of the sheet are removed. The sheet of scrim-containing solid hydrogel is affixed to the back side of a conductive silver/silver chloride snap, the front of which is embedded in a sheet of adhesive polyurethane foam with the top of the snap protruding therefrom. This configuration of conductive hydrogel, silver/silver chloride button and polyurethane foam, constitutes a test electrode unit. Two identical such electrode units are then joined together hydrogel back to hydrogel back to form an electrode pair. This electrode pair is then tested to determine its electrical responses for use as a medical electrode according to the proposed standards for pregelled ECG disposable electrodes by The Association for the Advancement of Medical Instrumentation (*Standard For Pregelled ECG Disposable Electrodes*, Association for the Advancement of Medical Instrumentation, February 1984 Revision). The guideline values specified by The Association for such electrode pairs in the following electrical measurements are:

| Electrical Characteristic | Standard Values |
|---|---|
| (a) Initial offset voltage V(0) (mV) | <100 |
| (b) Impedance at 10 Hz Z(10) (Ohm) Other important electrical characteristics which yield superior electrodes: | <3000 |
| (c) Impedance at 60 Hz Z(60) (Ohm) | <3000 |
| (d) Initial resting offset voltage V(IO) (mV) | — |
| (e) Ten second offset voltage V(10) (mV) | <100 |
| (f) Offset voltage after short V(S) (mV) | <100 |

The values obtained for the electrode pair of Example 1 are listed in Table III.

EXAMPLE 2

The hydrogel of this example is similar to that of Example 1, except that it is exposed to a different dose of radiant energy (0.76 Mrad). Subsequent samples are irradiated at 1.04, 1.09, 1.54, 1.80, and 2.10 Mrad respectively. The physical properties are described in Table I, above.

EXAMPLE 3

The hydrogel of this example is similar to Example except that the aqueous mixture is comprised of PVP (15 wt %), CMC (1.5 wt %), KCl (5 wt %), and biocides (<0.3 wt %). The extruded film is irradiated at a dose of 1.31 Mrad. It's physical and electrical properties are listed in Tables I and III, respectively.

EXAMPLE 4

The hydrogel of this example is similar to Example 3 except that the level of exposure to radiant energy is 1.0 Mrad. Subsequent samples are irradiated at 1.2 and 1.5 Mrad, respectively (See, Tables I and III).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A highly conductive non-stringy adhesive hydrophilic gel comprising a cohesive uniform aqueous mixture of poly(vinyl pyrrolidone) (PVP), a viscosity-enhancing hydrophilic polymer having a weight average molecular weight in excess of about 100 kilodaltons (kD), and an amount of a water-soluble electrolyte effective to reduce the transverse electrical resistance of said aqueous mixture to an impedance at 60 Hz of less than about 1,000 ohms, which aqueous mixture had been exposed to a dose of radiant energy effective to provide a highly conductive non-stringy adhesive hydrophilic gel which exhibits a sharp, substantially featureless force-displacement curve, having a force value of at least about 180 grams and an Adhesion Energy Density (AED) of at least about 5 to less than about 50 g/cm.

2. The hydrophilic gel of claim 1 which further comprises an additive uniformly dispersed therein.

3. The hydrophilic gel of claim 1 which further comprises an additive uniformly dispersed therein selected from the group consisting of preservatives, stabilizers, fire retardants, pigments, refractive particles, bacteriacides, antibiotics, cosmetics, moisturizers, pharmaceuticals, and mixtures thereof.

4. The hydrophilic gel of claim 1 which further comprises a biocide uniformly dispersed therein.

5. The hydrophilic gel of claim 1 which further comprises a low area-weight scrim in intimate contact therewith.

6. The hydrophilic gel of claim 1 which further comprises a low area-weight scrim in intimate contact therewith, which scrim is manufactured from a synthetic water-insoluble polymer.

7. The hydrophilic gel of claim 1 in which said viscosity-enhancing hydrophilic polymer is of a synthetic origin.

8. The hydrophilic gel of claim 1 in which said viscosity-enhancing hydrophilic polymer is of a natural origin.

9. The hydrophilic gel of claim 1 in which said viscosity-enhancing hydrophilic polymer is crosslinked.

10. The hydrophilic gel of claim 1 in which said viscosity-enhancing hydrophilic polymer is water-soluble.

11. The hydrophilic gel of claim 1 in which said viscosity-enhancing hydrophilic polymer is selected from the group consisting of polyacrylamide, poly(vinyl alcohol), polyacrylate, poly(ethylene oxide), poly(ethylene imine), carboxymethylcellulose, methylcellulose, polyacrylamide sulfonic acid, polyacrylonitrile, mixtures, blends, and copolymers thereof.

12. The hydrophilic gel of claim 1 in which said viscosity-enhancing hydrophilic polymer is poly(ethylene oxide).

13. The hydrophilic gel of claim 1 in which said viscosity-enhancing hydrophilic polymer is a cellulose derivative.

14. The hydrophilic gel of claim 1 in which said viscosity-enhancing hydrophilic polymer is carboxymethylcellulose.

15. The hydrophilic gel of claim 1 in which said viscosity-enhancing hydrophilic polymer is selected from the group consisting of agar, dextran, dextrin, carrageenan, xanthan, guar, derivatives, and mixtures thereof.

16. The hydrophilic gel of claim 1 in which said water-soluble electrolyte is an inorganic salt.

17. The hydrophilic gel of claim 1 in which said water-soluble electrolyte is selected from the group consisting of potassium salts, sodium salts, magnesium salts, calcium salts, and mixtures thereof.

18. The hydrophilic gel of claim 1 in which said water-soluble electrolyte is selected from the group consisting of potassium chloride, sodium chloride, magnesium sulfate, magnesium acetate, and mixtures thereof.

19. The hydrophilic gel of claim 1 in which said aqueous mixture had been exposed to a dose of radiant energy equivalent to greater than about 0.5 Mrad to less than about 4 Mrad.

20. The hydrophilic gel of claim 1 in which said aqueous mixture had been exposed to a dose of radiant energy equivalent to about 0.5 Mrad to less than about 2 Mrad.

21. The hydrophilic gel of claim 1 in which said aqueous mixture had been exposed to a dose of radiant energy equivalent to about 0.7 Mrad to about 1 Mrad.

22. The hydrophilic gel of claim 1 in which said PVP is present at a concentration of about 10 to about 35 weight percent.

23. The hydrophilic gel of claim 1 in which said viscosity-enhancing hydrophilic polymer is present at a concentration of about 0.5 to about 5 weight percent.

24. The hydrophilic gel of claim 1 in which said water-soluble electrolyte is present at a concentration of about 0.1 to about 10 weight percent.

25. The hydrophilic gel of claim 2 in which said additive is present at a concentration of about 0.001 to about 3 weight percent.

26. The hydrophilic gel of claim 1 in which said PVP has a weight average molecular weight in the range of about 500 kD to about 2,000 kD.

27. The hydrophilic gel of claim 1 in which said aqueous mixture has a viscosity of at least about 8,000 cps.

28. The hydrophilic gel of claim 1 in which said transverse electrical resistance of said aqueous mixture is reduced to an impedance at frequencies between about 10 to about 60 Hz of less than about 100 ohms.

29. A conductive wound dressing comprising a conductive non-stringy adhesive hydrophilic gel, which gel comprises a cohesive uniform aqueous mixture of poly(vinyl pyrrolidone) (PVP), a viscosity-enhancing hydrophilic polymer having a weight average molecular weight in excess of about 100 kilodaltons (kD), and a sufficient amount of a water-soluble electrolyte, which aqueous mixture had been exposed to a dose of radiant energy affective to provide a highly conductive non-stringy adhesive hydrophilic gel which exhibits a sharp, substantially featureless force-displacement curve, having a force value of at least about 180 grams and an Adhesion Energy Density (AED) of at least about 5 to less than about 50 g/cm.

30. A method of electrical wound healing which comprises (i) contacting an area of the body affected by a wound with the conductive wound dressing of claim 29 and (ii) applying an electrical impulse to said area with the aid of said conductive wound dressing for a period of time effective to promote healing.

31. An electrode comprising: (a) a highly conductive non-stringy adhesive hydrophilic gel, which gel comprises a cohesive uniform aqueous mixture of poly(vinyl pyrrolidone) (PVP), a viscosity-enhancing hydrophilic polymer having a weight average molecular weight in excess of about 100 kilodaltons (kD), and an amount of a water-soluble electrolyte effective to reduce the transverse electrical resistance of said aqueous mixture to an impedance at 60 Hz of less than about 1,000 ohms, which aqueous mixture had been exposed to a dose of radiant energy effective to provide a highly conductive non-stringy adhesive hydrophilic gel which exhibits a sharp, substantially featureless force-displacement curve, having a force value of at least about 180 grams and an Adhesion Energy Density (AED) of at least about 5 to less than about 50 g/cm; and (b) a conductive member, in intimate contact with said gel, to which may be connected external electrical apparatus.

32. The electrode of claim 31 which is further characterized by its ability to provide an intimate uniform contact and a low impedance such that the occurrence of burns on the skin is minimized, which burns may result from the use of such electrode under conditions suitable for ESU applications.

33. The electrode of claim 31 in which the amount of water-soluble electrolyte ranges from about 5 to about 8 percent by weight of said aqueous mixture to provide an electrode having a DC offset suitable for EKG measurements.

34. The hydrophilic gel of claim 1 having a force value of at least about 250 grams.

35. The hydrophilic gel of claim 1 having a force value of at least about 400 grams.

36. The conductive wound dressing of claim 29 in which said hydrophilic gel has a force value of at least about 250 grams.

37. The conductive wound dressing of claim 29 in which said hydrophilic gel has a force value of at least about 400 grams.

38. The electrode of claim 31 in which said hydrophilic gel has a force value of at least about 250 grams.

39. The electrode of claim 31 in which said hydrophilic gel has a force value of at least about 400 grams.

* * * * *

UNITED STATES PATENT AND TRADEMARK OFFICE
CERTIFICATE OF CORRECTION

PATENT NO. : 4,989,607

DATED : February 5, 1991

INVENTOR(S) : Keusch, et al.

It is certified that error appears in the above-identified patent and that said Letters Patent is hereby corrected as shown below:

The cover page, column 1, after item [76] and before item [21] should read --[73] Assignee: Nepera, Inc., Harriman, NY--

On the title page, after "Primary Examiner--Lee Cohen" and before item [57], should read --Attorney, Agent, or Firm--PENNIE & EDMONDS--.

Signed and Sealed this

Eighteenth Day of August, 1992

Attest:

DOUGLAS B. COMER

*Attesting Officer*     *Acting Commissioner of Patents and Trademarks*